United States Patent
Penning De Vries (10) Patent No.: US 11,213,218 B2
(45) Date of Patent: Jan. 4, 2022

(54) MEASUREMENT OF SKIN CONDUCTANCE

(71) Applicant: KONINKLIJKE PHILIPS N.V., Eindhoven (NL)

(72) Inventor: Hendricus Theodorus Gerardus Maria Penning De Vries, Mierlo (NL)

(73) Assignee: Koninklijke Philips N.V., Eindhoven (NL)

( * ) Notice: Subject to any disclaimer, the term of this patent is extended or adjusted under 35 U.S.C. 154(b) by 509 days.

(21) Appl. No.: 16/303,321

(22) PCT Filed: May 12, 2017

(86) PCT No.: PCT/EP2017/061447
§ 371 (c)(1),
(2) Date: Nov. 20, 2018

(87) PCT Pub. No.: WO2017/202626
PCT Pub. Date: Nov. 30, 2017

(65) Prior Publication Data
US 2019/0209041 A1 Jul. 11, 2019

(30) Foreign Application Priority Data

May 25, 2016 (EP) .................................. 16171377

(51) Int. Cl.
*A61B 5/0531* (2021.01)
*A61B 5/00* (2006.01)
(Continued)

(52) U.S. Cl.
CPC .......... *A61B 5/0531* (2013.01); *A61B 5/0533* (2013.01); *A61B 5/165* (2013.01);
(Continued)

(58) Field of Classification Search
CPC ..... A61B 5/0531; A61B 5/721; A61B 5/7225; A61B 5/0533; A61B 5/165; A61B 5/4815;
(Continued)

(56) References Cited

U.S. PATENT DOCUMENTS 6,167,299 A * 12/2000 Galchenkov ......... A61B 5/0533
600/547
9,962,104 B2 5/2018 De Vries et al.
(Continued)

FOREIGN PATENT DOCUMENTS

| WO | 2002013690 A1 | 2/2002 |
| WO | 2014140960 A1 | 9/2014 |
| WO | 2017178359 A1 | 10/2017 |

OTHER PUBLICATIONS

Benedek et al., "Decomposition of skin conductance data by means of nonnegative deconvolution", 2010, Psychophysiology, 47, pp. 647-658 (Year: 2010).*

(Continued)

*Primary Examiner* — Sean P Dougherty
*Assistant Examiner* — Kyle W. Kretzer (57) ABSTRACT

A sensor is configured for measuring skin conductance. An amplifier is used to convert the skin conductance into an analog output voltage which is then converted into the digital domain by an analog-to-digital converter, so that an increase in the tonic skin conductance and the phasic skin conductance response are obtained in the digital domain. The amplifier has a non-linear logarithmic gain, with a decreasing gain for increasing skin conductance values. The sensor enables detection of increases in both tonic and phasic signals over a wide range of skin conductance. This allows the use of a lower resolution, and therefore lower cost, analog-to-digital converter.

18 Claims, 4 Drawing Sheets

(51) Int. Cl.
| | |
|---|---|
| *A61B 5/0533* | (2021.01) |
| *H03G 7/08* | (2006.01) |
| *A61B 5/16* | (2006.01) |
| *G01N 27/04* | (2006.01) |
| *A61B 5/01* | (2006.01) |
| *A61B 5/11* | (2006.01) |
| *A61M 21/02* | (2006.01) |
| *A61M 21/00* | (2006.01) |

(52) U.S. Cl.
CPC .......... *A61B 5/4815* (2013.01); *A61B 5/6824* (2013.01); *A61B 5/721* (2013.01); *A61B 5/7207* (2013.01); *A61B 5/7225* (2013.01); *A61B 5/7282* (2013.01); *A61M 21/02* (2013.01); *G01N 27/041* (2013.01); *H03G 7/08* (2013.01); *A61B 5/01* (2013.01); *A61B 5/11* (2013.01); *A61B 5/441* (2013.01); *A61B 5/681* (2013.01); *A61B 2560/0252* (2013.01); *A61M 2021/0011* (2013.01); *A61M 2205/50* (2013.01); *A61M 2230/65* (2013.01)

(58) Field of Classification Search
CPC ... A61B 5/6824; A61B 5/7207; A61B 5/7282; A61B 5/441; A61B 5/01; A61B 5/681; A61B 5/11; A61B 2560/0252; A61B 5/053; A61M 21/02; A61M 2021/0011; A61M 2205/50; A61M 2230/65; H03G 7/08; G01N 27/041; H03F 3/45475
See application file for complete search history.

(56) References Cited

U.S. PATENT DOCUMENTS

| | | |
|---|---|---|
| 2008/0208016 A1 | 8/2008 | Hughes et al. |
| 2010/0268056 A1 | 10/2010 | Picard et al. |
| 2012/0158311 A1 | 6/2012 | Levenstein et al. |
| 2014/0031704 A1* | 1/2014 | De Vries .................. A61B 5/72 600/485 |
| 2014/0228666 A1 | 8/2014 | Ausin Sanchez et al. |
| 2014/0288401 A1 | 9/2014 | Ouwerkerk et al. |
| 2014/0329214 A1* | 11/2014 | Bitoun ............... A61B 5/02055 434/262 |
| 2015/0297145 A1 | 10/2015 | Luna et al. |

OTHER PUBLICATIONS

Braithwaite et al., "A Guide for Analysing Electrodermal Activity (EDA) & Skin Conductance Responses (SCRs) for Psychological Experiments", 2015, University of Brimingham, UK, 2nd version, pp. 1-43 (Year: 2015).*

De Vries, G. et al., "Enhanced method for robust mood extraction from skin conductance", Proceedings of the Third International Conference on Bio-inspired Systems and Signal Processing, pp. 139-144, 2010.

* cited by examiner

MEASUREMENT OF SKIN CONDUCTANCE

CROSS-REFERENCE TO PRIOR APPLICATIONS

This application is the U.S. National Phase application under 35 U.S.C. § 371 of International Application No. PCT/EP2017/061447, filed on 12 May 2017, which claims the benefit of European Patent Application No. 16171377.1, filed on 25 May 2016. These applications are hereby incorporated by reference herein.

FIELD OF THE INVENTION

This invention relates to the measurement of skin conductance.

BACKGROUND OF THE INVENTION

It is well known that skin conductance changes when a person sweats, and that such sweating may be brought about either by physical effort or by the emotional state of a person.

For example, the applicant is developing a wristband type system which can determine an emotional state of the wearer from skin conductance measurements. This information may then be used to advise the user to undertake physical action or to relax, with the aim of improving the sleep efficiency of the wearer.

An increase in skin conductance is the result of sweating that fills the sweat glands with salty sweat. Filled sweat glands form a conductance path to bloodstreams beneath, the latter having very high conductance. The skin conductance can be measured by placing electrodes on the skin, applying a voltage and measuring the current.

Sweating is partly caused by the body temperature regulation process, and partly by an effect that depends on the user's emotional state. Both effects take place at the same time, and they combine to result in an overall skin conductance. The so-called tonic skin response or skin conductance level (SCL) is a response which varies relatively slowly over time and depends both on temperature regulation and emotional conditions. The so-called phasic response or skin conductance response (SCR) (or galvanic skin response (GSR)) is a response which varies relatively quickly over time and depends on the emotional triggers. It is difficult to separate the temperature regulation effect from the emotional effect.

The emotional state of a user is generally the result of emotional triggers that have happened in the recent past. These emotional triggers result in the more short term phasic variations in the skin conductance. These phasic responses are minimally dependent on body temperature related processes. However, they have relatively small amplitude and are easily disturbed by user wrist movements that influence the skin-electrode contact pressure.

The contribution of emotional effects, temperature regulation and motion effects to a skin conductance measurement also depends on the location of the measurement. For example, the emotional component is more pronounced at the finger tips. At less pronounced areas such as the base of the wrist, or even more so at the top of the wrist, the emotional component becomes small and it is more difficult to separate emotional components from temperature regulation component or motion disturbances.

A pure skin conductance measurement device cannot distinguish between the emotional component of the tonic response and the thermal regulation component. The measurement will see the effect of all conductance variations in parallel.

The emotional component is related to cortisol levels, which is an adrenal hormone essential to the maintenance of homeostasis. Called "the stress hormone", cortisol influences, regulates or modulates many of the changes that occur in the body in response to stress. Cortisol levels normally fluctuate throughout the day and night in a circadian rhythm that peaks at about 8 am and reaches its lowest around 4 am. More cortisol is secreted in response to stress.

A skin conductance sensor typically applies a voltage (or current) to the skin, and measures a resulting response. This response may be a current flowing though (or a voltage across) the skin. In the latter case, voltage is applied to the skin through a series resistor, so that the skin and the series resistor function as a variable voltage divider. A current flowing is measured using a current amplifier and a voltage is sensed using a voltage amplifier.

The sensor may use a single ended design or a differential design. A single ended design is of lower cost and less sensitive to noise. A differential design is more complex but enables common mode effects to be cancelled.

Figure 1:
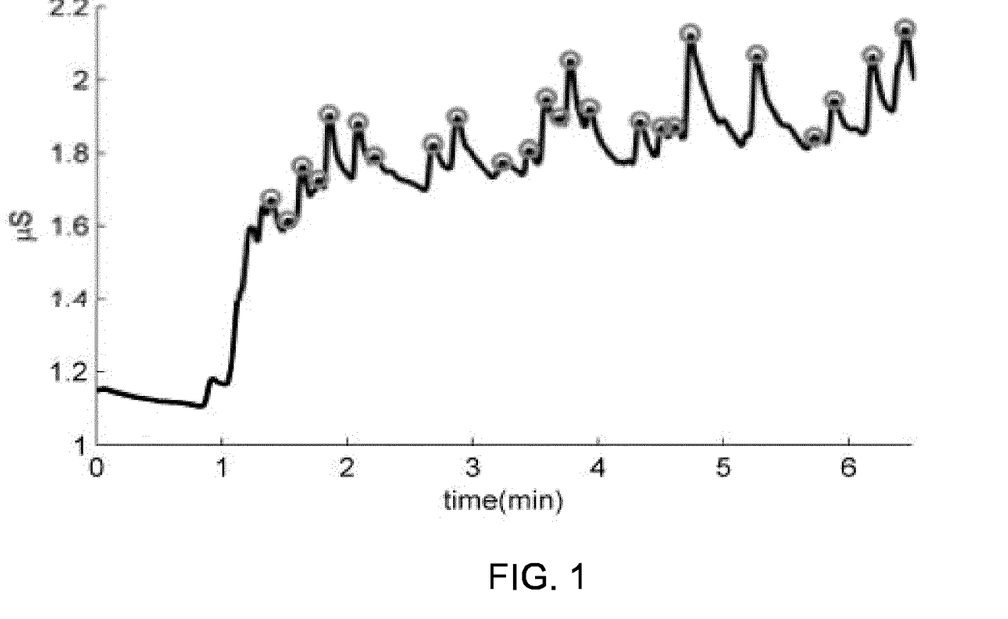
FIG. 1 shows a skin conductance over time.

FIG. 1 shows a typical skin response as conductance versus time. In this graph, the skin conductance level in the form of the average trend can be distinguished from the (phasic) skin conductance response SCR components, which are the high frequency peaks.

A sensor device which measures skin conductance needs to be able to provide separation of these two components using signal processing, if actions are to be taken in response to the emotional state alone.

Human skin conductance values vary over a wide range. Known skin conductance sensor designs cover the full range of skin conductance values, at high resolution. This requires the use of highly accurate amplifiers and high resolution analog-to-digital converters (ADCs). Some designs use 24-bit conversion. Such sensors become expensive and not suited for use in commercial products.

There is therefore a need for a system for measuring and processing skin conductance values in a manner that enables the phasic component to be extracted, and which can be implemented at low cost and with simple signal processing.

SUMMARY OF THE INVENTION

The invention is defined by the claims.

According to examples in accordance with an aspect of the invention, there is provided a sensor for measuring skin conductance, comprising:

an amplifier for converting the skin conductance into an analog output voltage;

an analog to digital converter for converting the analog output voltage to a digital output signal; and a digital processor for extracting the phasic skin response from the digital output signal and increases in the tonic skin response, wherein the amplifier has a logarithmic gain for generating an output signal which is a logarithm of the skin conductance, thereby with a decreasing gain for increasing skin conductance values.

The overall tonic skin response may be obtained as one output of the system. Emotional triggers will induce an increase in skin conductance, so activities in phasic skin response are used as indicators for identifying the increase of the emotional part of the tonic component.

The invention provides an improved electrical circuit for the detection of skin responses. The sensor enables detection of the overall tonic (i.e. SCL) response and separation of the phasic (i.e. SCR) signals and over a wide range of skin conductance. The invention is based on the recognition that the ratio of SCR and SCL amplitudes has a similar order of magnitude independent of the absolute skin conductance value. For optimal use of an analog to digital converter, a quantization level is desired which is optimally independent of the magnitude of the skin conductance. The logarithmic gain of the amplifier enables more efficient use of the analog to digital converter over the range of skin conductance values, and may thus enable a lower resolution and therefore lower cost converter to be used. Higher performance can still be reached when a high resolution analog to digital convertor is used. The invention in particular ensures that the digitized signal gives the same ability to extract the phasic component from the tonic signal for all input skin conductance levels. A conventional linear analog to digital converter instead needs to be designed to give a required resolution at low skin conductance levels, but at higher skin conductance values, the resolution is unnecessarily high.

The sensor enables the use of fewer components and/or components that can have relaxed specifications. This allows for lower cost, low power and small size implementations, suitable for a high performance consumer product.

The logarithmic function of gain with respect to the skin conductance means that small skin conductance values produce signals of a first amplitude to the analog to digital converter, while larger conductance values produce signals which are larger, but not larger in the same proportion, to the analog to digital converter. The measurement signal is thus amplified in such a way for the analog to digital converter that the skin conductance signal properties for detection of phasic values are optimally preserved.

The digital processor is for example adapted to extract the phasic skin response by:
  detecting local maxima and minima in the digital output signal representing the skin conductance
  detecting rising edges in the digital output signal representing the skin conductance;
  identifying as the phasic skin response those the rising edges that have a duration within a first range and an amplitude change within a second range,
and the digital processor is adapted to extract increases in the tonic skin response by:
  detecting rises in the digital output signal representing the skin conductance over a period at least longer than the maximum of the first range.

Thus, short duration rises in skin conductance are determined to be phasic responses whereas slower rises are determined to be caused be increases in tonic skin response.

The digital processor is for example adapted to extract increases in the tonic skin response by filtering out rises in the digital output signal representing the skin conductance corresponding to rising edges identified as phasic skin response. Thus, the tonic increase is determined by filtering out phasic responses.

The amplifier for example comprises an operational amplifier having a reference voltage at a first input, a second input (virtually at the same voltage as the first input), a skin conductance between the second input and ground and an output voltage at an output, wherein a feedback path is provided between the output and the second input which includes at least one diode. A current flows from the output, through the diode, through the skin conductance to ground. This diode in a feedback path has a logarithmic relationship between voltage drop and current, and this provides the desired logarithmic gain of the amplifier. The feedback path functions to convert current flowing through the skin to a voltage at the output of the operational amplifier.

The first input is for example the non-inverting input of the operational amplifier and the second input is the inverting input. The feedback path is thus a negative feedback path.

The analog to digital converter is for example a 12 bit converter. A lower number of bits is made possible by the more efficient use of the analog to digital converter.

The sensor may further comprise a temperature correction circuit. This may be used to compensate for the temperature dependency of the analog components which provide the desired non-linear gain, such as the feedback diode or diodes.

The sensor may comprise a signal processing unit for filtering out skin conductance measurements during events of poor skin electrode contact and/or for filtering to reject false responses due to motion detected by an accelerometer. These filtering approaches improve the quality of the collected skin conductance data.

A processor may be used for calculating a cortisol response from the skin responses.

Activities in the phasic skin response and also increases in the tonic component are indicators for emotional triggers in the recent past and may be used as inputs for cortisol predication. When phasic responses are available, these are most clean as they are not polluted by thermal effects. In the absence of phasic skin responses, an increase in the tonic response component may be used as an indicator of a cortisol response.

The invention also provides a monitoring system comprising:
  a wrist band; and
  a sensor as defined above mounted on the wrist band for application to the top of the wrist.

The top of the wrist (i.e. where a watch face is typically mounted) gives a relatively poor phasic signal. By employing the sensor design defined above, the separation of phasic and tonic signals becomes practical even with a low cost sensor architecture.

An output device may be provided for providing advice to the user relating to required behavior for improving the quality of a next sleep period of the user. The sensor is thus used to improve sleep efficiency of the user of the monitoring system.

Examples in accordance with another aspect of the invention provide a method of measuring skin conductance, comprising:
  performing signal amplification to convert a skin conductance into an analog output voltage;
  converting the analog output voltage to a digital output signal; and
  extracting the phasic skin response from the digital output signal and increases in the tonic skin response,
  wherein the amplification is implemented with a logarithmic gain, generating an output signal which is a logarithm of the skin conductance, thereby with a decreasing gain for increasing skin conductance.

This method provides a digital output signal from which the different skin responses can be extracted in an efficient manner, regardless of the skin conductance level.

The amplification is implemented with a logarithmic function of gain with respect to the skin conductance. 12 bit analog to digital conversion may be used, and there may be temperature correction to compensate for temperature dependence of the non-linear gain.

Extracting the phasic skin response may comprise:
detecting local maxima and minima in the digital output signal representing the skin conductance;
detecting rising edges in the digital output signal representing the skin conductance;
identifying as the phasic skin response those the rising edges that have a duration within a first range and an amplitude change within a second range,
and extracting the tonic skin response may comprise:
detecting rises in the digital output signal representing the skin conductance over a period at least longer than the maximum of the first range.

The tonic skin response may be obtained by filtering out rises in the digital output signal representing the skin conductance corresponding to rising edges identified as phasic skin response.

A monitoring method may comprise measuring skin conductance at the top of the wrist by applying the method as defined above using a wrist band sensor. The monitoring method may be used to provide advice relating to required behavior for improving the quality of a next sleep period.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a sensor for measuring skin conductance. An amplifier is used to convert the skin conductance into an analog output voltage which is then converted into the digital domain, so that the overall skin response is obtained in the digital domain. The amplifier has a non-linear logarithmic gain, with a decreasing gain for increasing skin conductance values. The sensor enables separation of the phasic and tonic signals over a wide range of skin conductance. It provides optimal use of the analog to digital converter so that a lower resolution and therefore lower cost converter can be used.

Conventional skin conductance sensor designs cover the full range of skin conductance values at high resolution. That requires the use of highly accurate amplifiers and high resolution analog-to-digital converters, for example 24-bit conversion. Such sensors become expensive and not suited for use in commercial products.

The invention is based on the recognition that the ratio of phasic to tonic (overall) skin response amplitudes is approximately constant. This means that a lower resolution (i.e. quantization step size) is needed at higher skin conductivities, in order for the phasic skin response to be separated with the same resolution.

Figure 2:
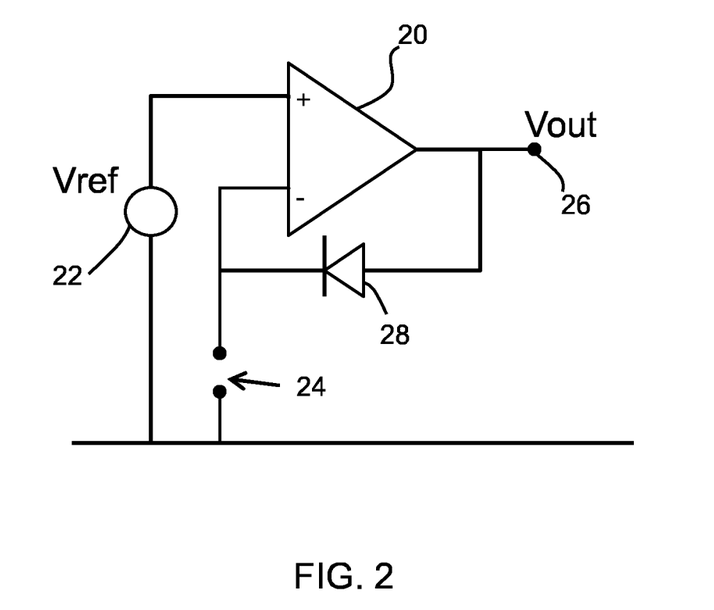
FIG. 2 shows a logarithmic amplifier.

FIG. 2 shows a circuit diagram for a logarithmic amplifier. The circuit comprises an operational amplifier 20 having a reference voltage Vref (shown as voltage source 22) at the non-inverting input, and the input voltage 24 to be amplified at the inverting input. There is a negative feedback path between the output 26 and the inverting input in the form of a diode 28.

The relationship between the diode voltage and current is given by:

$$V_{FWD} = n * V_T * \ln(1 + I_{FWD}/I_S) \qquad (\text{Eq. 1})$$

Where $V_{FWD}$ is the forward diode voltage drop, $I_{FWD}$ is the forward current, n is the emission coefficient, $V_T$ is the thermal voltage, $I_S$ is the saturation current. $V_T = k*T/q$, where k is the Boltzmann constant, T is the absolute temperature and q is the charge of an electron.

The overall circuit provides an output:

$$Vout = Vref + n * V_T * \ln(1 + Vref * Gskin/I_S) \qquad (\text{Eq. 2})$$

Where Gskin is the skin conductance connected between electrodes 24.

Note that a signal representing the skin conductance may be amplified, or else the skin current (for a given applied voltage) may be amplified. These each represent the skin conductance and may thus be considered to comprise skin conductance signals.

This circuit thus has a gain which is a logarithmic function of the magnitude of the input parameter 24 to be amplified. Thus, when the amplified output is provided as input to an analog to digital converter, as the input signal increases, there are progressively larger steps in the size of the input signal before the next conversion threshold of the analog to digital converter is reached.

Figure 3:
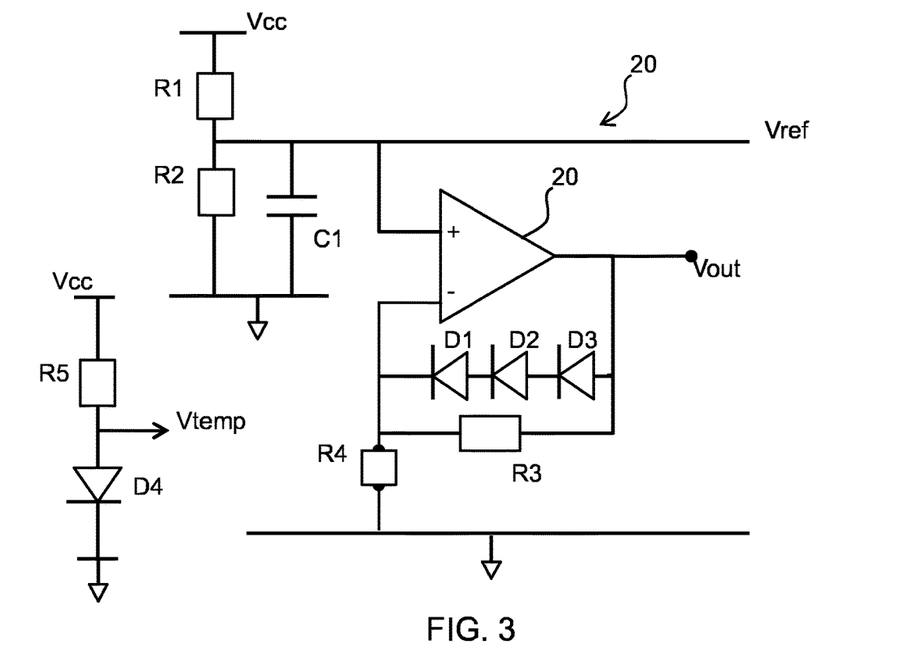
FIG. 3 shows a first example of a skin conductance sensor.

FIG. 3 shows part of a sensor for measuring skin conductance, based on the logarithmic amplifier circuit. FIG. 3 shows the analog domain parts of the sensor, in particular an analog amplifier circuit 30.

The amplifier circuit 30 is for converting the skin conductance into an analog output voltage Vout. It is the front end amplifier, in that one of the inputs to the amplifier makes direct contact with the skin, in particular the inverting input in the example shown.

The reference input Vref is provided by a potential divider between a supply rail Vcc and ground, formed by resistors R1 and R2. For example, the reference voltage Vref may be 500 mV. A smoothing capacitor C1 is at the output.

The negative feedback path comprises a series set of three diodes D1, D2, D3 in the example shown, in the forward direction between the output and the inverting input. This converts the current flowing through the skin to a voltage at the non-inverting input to the operational amplifier. Three diodes are used to increase the gain of the system so that the amplifier output signal matches the analog digital convertor range over the desired skin conductance range.

A resistor R3 is in parallel with the diode string. Resistor R3 can be desired to make the circuit work in practice and sinks input currents from the operational amplifier in particular when there are very low skin conductance values. In an alternate implementation, a resistor to sink the operational amplifier input currents may be placed in parallel with the skin conductance, which is represented by resistor R4 in FIG. 3.

FIG. 3 also shows a temperature measurement circuit. This is used because the transfer function of the non-linear diodes is dependent on temperature. It comprises a resistor R5 and a diode D4 in series between the voltage rail Vcc and ground. A temperature dependent voltage Vtemp is present at the junction between the resistor R5 and diode D4. This temperature dependent voltage is read out by an overall system micro controller and used for temperature compensation.

The resistor R5 is chosen so the current through the diode D4 is equal to the current that would flow through a reference skin conductance, such as 100 kΩ.

The current $I_{FWD}$ through diode D4 depends on its forward voltage $V_{FWD}$:

$$I_{FWD}=(Vcc-V_{FWD})/R5 \qquad (Eq.\ 3)$$

$V_{FWD}$ is measured, and $I_{FWD}$ can be obtained from Eq. 3. By then substituting into Eq. 1, the temperature dependency $n*k*T/q$ or a measure of actual temperature T can then be obtained.

Processing equations in this way is a complex process for an embedded microprocessor. However, it is known beforehand that the voltage over diode D4, with a small diode current, is in the range of 0.5V. This is much lower than Vcc and because of that the current through the diode can be estimated by:

$$I_{FWD}\sim(Vcc-0.5)/R5 \qquad (Eq.\ 4)$$

This enables an approximation of the voltage over diode D4 to be used (i.e. $V_{FWD}$ in Eq. 1, equivalent to Vtemp in FIG. 3).

This means that iterative calculations can be avoided to provide simpler processing.

An estimate for the temperature and emission coefficient can then be obtained from:

$$T\sim=q/(n*k)*\text{Vtemp}/\ln(1+I_{FWD}/I_S) \qquad (Eq.\ 5)$$

$$nkT/q\sim=\text{Vtemp}/\ln(1+I_{FWD}/I_S) \qquad (Eq.\ 6)$$

All signals Vout, Vref and Vtemp are digitized by an analog to digital convertor. Calculations to estimate Gskin from Vout and T are then executed in the micro controller.

In an implementation where there are N diodes in series (N=3 in FIG. 3) the signal Vout becomes:

$$V\text{out}=V\text{ref}+N*nV_T*\ln((G\text{skin}*V\text{ref})/I_S+1) \qquad (Eq.\ 7)$$

By rearranging, an estimate for the skin conductance estimation from the measured output voltage may be obtained using:

$$G\text{skinEst}=I_S/V\text{ref}*(\exp((V\text{out}-V\text{ref})/(N*nV_T))-1 \qquad (Eq.\ 8)$$

It can be assumed that Vref has a specific value or else it can be measured with an analog to digital converter.

The general operation of the circuit is to apply a voltage to the skin. As a response, a current flows through the skin. The diode converts this current into an amplifier output voltage that is measured with an analog to digital convertor. A micro controller converts the analog to digital convertor reading into an estimate GskinEst for the actual skin conductance Gskin.

Temperature variations may or may not be taken into account. If thermal effects are ignored, $nkT/q$ can be treated as a constant and the temperature compensation circuit is not needed. The temperature compensation circuit allows an estimate of $nV_T$ and is sufficient for medium accuracy temperature compensation.

Another option is to measure the temperature T with a dedicated temperature sensor circuit and then calculate $nV_T$ with an assumed value for n.

Figure 4:
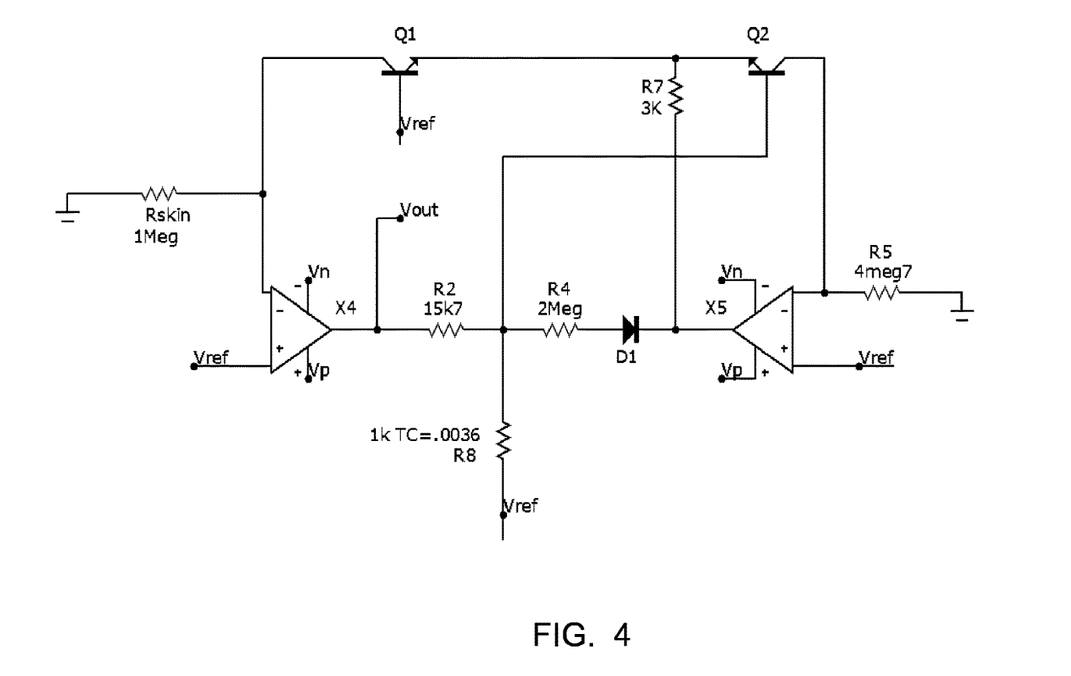
FIG. 4 shows a second example of a skin conductance sensor.

FIG. 4 shows an alternative circuit which provides more accurate temperature compensation. It has improved temperature stability.

The circuit comprises two operational amplifiers 20a, 20b each with the reference voltage Vref applied to the non-inverting terminal. It comprises transistors Q1, Q2 as well as diode D1 and thus has significantly more components. The circuit can be more accurate in temperature behavior and easier to design with respect to the gain configuration. It is another version of a logarithmic sensor implementation.

Figure 5:
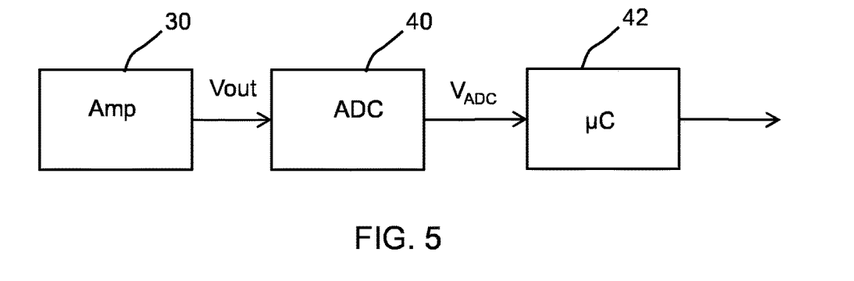
FIG. 5 shows a system for determining skin conductance using the sensor of FIG. 3.

As shown in FIG. 5, the output Vout from the amplifier circuit 30 (e.g. of FIG. 3 or FIG. 4) is provided to an analog to digital converter 40, and a digital processor 42 takes the digital output and then calculates the skin conductance:

$$G\text{skinEst}=(I_S*(\exp((V_{ADC}-V_{ref})/(N*nV_T))-1))/V\text{ref} \qquad (Eq.\ 9)$$

Vout (used above in Eq. 8) is the actual analog output voltage from the sensor whereas $V_{ADC}$ is the analog voltage calculated back from the ADC reading. In theory, both have the same value, but in practice there can be a difference due to offsets, noise, component tolerances Eq. 9 applies in case there is no need for temperature correction and $nV_T$ is handled as a constant.

If there is a need for temperature compensation:

$$G\text{skinEst}=I_S/V\text{ref}*(((Vcc\sim V_{FWD})/(I_S*R5))^\wedge \\ ((V\text{out}-V\text{ref})/(N*V\text{temp}))-1)) \qquad (Eq.\ 10)$$

Eq. 10 applies in case there is a need for medium accuracy temperature correction and $nV_T$ is measured according to Eq. 5 and Eq. 6. Substitution of Eq. 4 into Eq. 6 and into Eq. 9 leads to Eq. 10.

The digital signal processor is able to detect both tonic (i.e. increase in SCL) and phasic (i.e. SCR) signals and over a wide range of skin conductance. By providing the analog to digital converter with a logarithmically amplified signal, the quantization steps become optimally dependent on the magnitude of the skin conductance.

Figure 6:
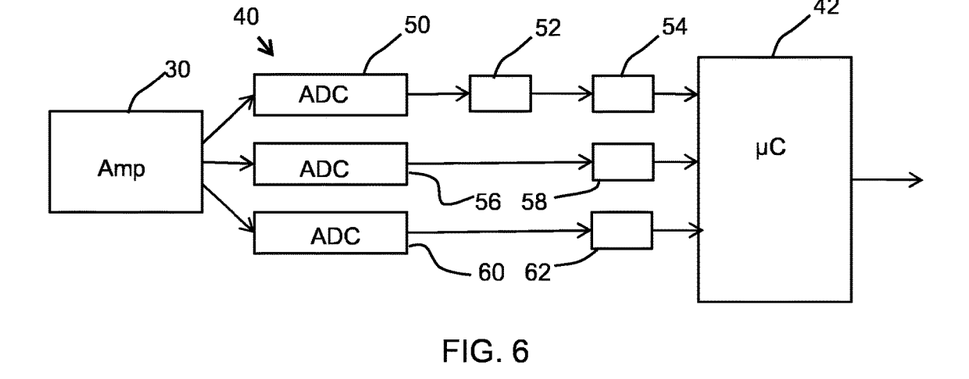
FIG. 6 shows the analog to digital conversion and filtering process in more detail.

The signal processing is shown in more detail in FIG. 6. The amplifier 30 is the analog frontend.

The analog to digital converter 40 has front end analog to digital conversion of three channels.

A first channel is the sensor output signal, which is converted at 12 bits with a sampling rate of 160 Hz in unit 50 and processed digitally in unit 52 to correct for contact bounce. The 160 Hz conversion is much higher than the maximum frequency of interest, but it improves detection of contact bounce. Skin-electrode contacts sometimes break when the user moves his wrist. The effect on the measured signal has the amplitude of the SCL signal (the skin conductance drops temporarily to 0), while the interest is in measuring SCR that is much smaller than SCL.

The impulse response of an analog filter on the signal will be significantly larger than the SCR being measured. Therefore analog filtering to remove contact bounce would destroy SCR information.

In the digital domain, in unit 52, the effect of a broken contact is resolved in a more effective way. This correction is based on level detection and edge detection to detect signal dropout and then limit the effect of signals captured during such a dropout event on the further signal processing.

A low pass filter 54 with a cut off of around 5 Hz acts as an aliasing filter. The signal is then decimated to 10 Hz (which may be considered to take place in filter 54), which is the sample rate of interest. Signals being detected as dropout signals in unit 52 can be reduced by replacement with the last valid signal value.

A second channel is the reference voltage. It is converted at 12 bits with a sampling rate of 160 Hz or slower in unit 56. A low pass filter 58 filters the reference signal and optionally decimates the signal values to 10 Hz which is the sample rate of interest.

A third optional channel is the temperature signal. It is converted at 12 bits with a sampling rate of 10 Hz or slower. Temperature data is low pass filtered by filter 62 with a cut off of 0.1 Hz.

The signal processing takes place in unit 42 which comprises conversion from the voltage domain to the conductance domain.

In order to prevent long impulse responses after bad contact events, the logarithmic frontend 30 has no specific bandwidth limitation and provides a bandwidth greater than 160 Hz.

The system may also comprise an accelerometer, for example that operates at a 10 Hz sample rate. A motion signal is derived from the accelerometer data and a threshold is applied. Three-axis accelerometer signals are processed to derive a motion detection signal when a movement threshold is passed. This may be based on a summation of the absolute values of the derivatives of the accelerometer signals.

Motion detection will take place after the start of the motion. Thus, motion artifacts are filtered out by delaying the skin conductance detection signal and aligning the motion detection signal with the delayed detection signal. If the data is determined to be invalid based on the motion detection signal, the previous valid data is used to replace the invalid data so that no corrupted data is passed on for further signal processing.

Figure 7:
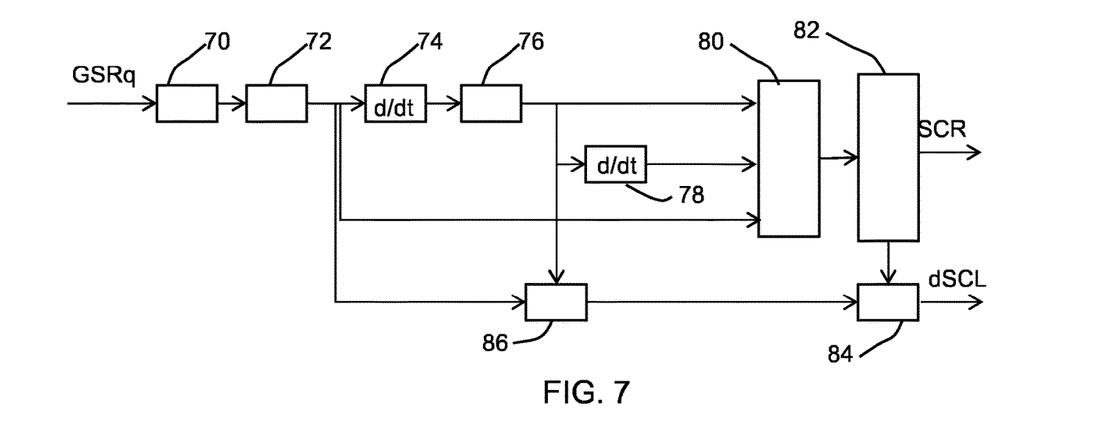
FIG. 7 shows how the skin conductance is processed to derive a separate phasic component.

FIG. 7 shows how the detection of phasic responses and detection of increases in tonic skin conductance level are obtained. The increase in tonic response is denoted dSCL. Furthermore, the signal dSCL represents a detected increase in the skin conductance that is determined as not being attributable to a phasic SCR response. In this way, it can be used as a filter for separating the overall response into the tonic and phasic components.

The input GSRq is the GSR skin measurement with a signal quality improvement obtained by the motion artifact filtering explained above. Thus, it is a digital signal which has already undergone the analogue logarithmic amplification. The outputs are dSCL which represents any rise of skin conductance in a period of 1 minute not attributable to a phasic response, and therefore forming part of a general rise in the slower tonic response.

First there is a low pass filter 70 that filters the skin conductance signal at a bandwidth of approximately 1 Hz and a sample rate of 10 Hz. Then the signal is decimated to approximately 3 Hz in the decimator 72. The output of the decimator 72 is the overall skin conductance signal.

The derivative of the skin conductance signal is calculated in the derivative unit 74. The output of the derivative unit 74 is the derivative of this skin conductance signal. The signal polarity of this signal indicates a rising/falling edge of the skin conductance signal. The sign is determined in unit 76. A rising edge is indicative of a phasic response. The output is a binary signal I/O. A decreasing skin conductance is not of interest for identifying the phasic response, since the phasic response relaxes slowly.

A sign change in the first derivative of the skin conductance signal indicates a relative minima and maxima in the skin conductance signal, i.e. a local (phasic) peak or trough. A second derivative unit 78 is provided for this purpose. If the output of unit 76 changes sign, a local maxima or minima has been reached. The output of the unit 78 provides a pulse when the sign of the derivative changes and the output is a binary signal I/O with a 1 pulse at each sign change.

An edge detection module 80 captures specific times and values in the skin conductance signal. These timing and amplitude values are discussed below (Tonset, Aonset, Tstart, Astart, Tend, Aend). The module is implemented as a state machine.

A flag/quality input signal follows the same path as the data. This signal is used to inform the signal processing modules about the reliability of the signal. It is first generated in the digital processing module 52 when dropouts are detected. Next it is updated in the low pass filter (and decimating unit) 54. It is modified when user motion is detected. Finally it is passed via module 70 and 82 (described below) where it can influence SCR detection.

In this way, the detected SCR signal has a quality assigned that is derived from analysis of the skin electrode contact quality.

During a bad contact event, the analogue to digital converter signal drops below a threshold. Furthermore, there are sharp edges when the electrodes make or break skin contact. The values recorded by the analog to digital converter however start to drift before the first detection is made at the threshold. This happens because the electrode-skin force decreases. During the drift phase, the signal quality changes from acceptable to poor. A similar effect arises after the last detection, in that the output of the analog to digital converter drifts to a stable end value when the electrode-skin force moves to its final value. In this phase signal quality changes from poor to acceptable. The transition of the signal quality is thus not stepwise but there is a smooth transition.

When a wristband incorporating the sensor is worn at the bottom of the wrist, there is a relatively small phasic signal with relative large disturbances. For this reason, all signal detail is preserved and soft decision methods are employed by adding a signal qualifier.

The quality indicator follows the data with the same filtering operations, and is used to provide an indication that reliable data has been collected. With a soft decision methods, the signal qualifier can be used to weight individual detected phasic (SCR) contributions in a final summation result (e.g. over one minute as explained above).

In this way, a quality of a detected edge (i.e. an indication of whether it is caused by changes in contact quality or caused by a phasic skin response) can be derived by combining all data used during detection.

A determination module 82 filters out rising edges from the signal that do not conform to a particular specification:

SCR duration (time between a maxima and a minima) is within specific minimum and maximum limits;

SCR amplitude change (between the a maxima and minima) is within specific minimum and maximum limits; and SCR quality should exceed a minimum value.

An SCR or phasic response can be detected by the determination module 82 as a period of monotonic rise of the skin conductance signal. Such a monotonic rise has a duration and an amplitude. The rising edge starts when the first increase in signal is detected (at a start time Tonset and with an amplitude Aonset). It ends when the last increase in signal has been detected (at an end time Tend and with an amplitude Aend). Another timing moment of interest occurs when the signal level crosses a level dependent on the onset amplitude (Time Tstart and amplitude Astart=(1+k)*Aonset).

The signal rise time can be determined by the subtraction Trise=Tend~Tstart.

A rise in signal is qualified as phasic response when it has a rise time between certain minimum and a maximum values.

An example of SCR detection criteria are:

Rising edge 1 sec <Trise <2.5 sec with amplitude 0.2<k<0.5

An example of SCL detection criteria (for attributing rises in skin conductance to a tonic response) are:

Any increase in skin conductance, with a rise time longer than the SCR criteria (with no amplitude constraints involved).

The qualification of a skin conductance rise as a phasic response is based on a factor k, with Tstart being detected when the signal amplitude has risen from Aonset to Astart= (1+k)*Aonset. This is a part of the reason why logarithmic amplification and analog to digital conversion preserves the phasic response detection properties of the system.

An enabling unit 86 passes only rising parts of the skin conductance signal. A determination unit 84 then determines dSCL, the total rise in skin conductance signal for periods when no SCR (phasic response) has been detected.

In particular, the determination unit 84 filters out signals relating to rises in skin conductance that are not caused by a phasic response. The module 82 controls determination unit 84 to output the rises in skin conductance during the period of rising skin conductance where no SCR was detected.

In particular, the detected SCR signal is used as part of the determination of the dSCL signal in unit 84. The enabling unit 86 is a gate that outputs an increase in skin conductance (which equals the output of unit 72 when unit 76 identifies an increase or zero when unit 76 identifies no increase). The determination unit 84 is a gate that passes the output of 86 when no phasic SCR response is detected. They are longer rise time portions of the skin conductance signal.

The dSCL output indicates rises in the skin conductance which are not caused by a phasic response. This information may be used by a cortisol processing unit which then derives an estimation of cortisol levels to provide a cortisol trace for the user, for example using the approach of US 2014/0288401. This discloses the use of a sum of SCR signals, with an option to add an indication of a rising SCL level as input.

Figure 8:
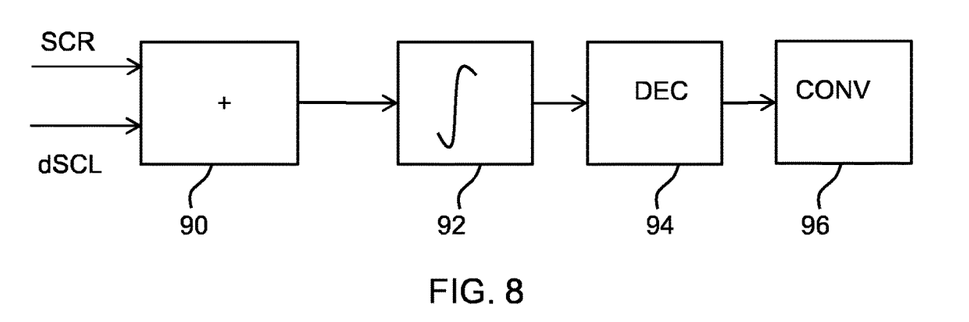
FIG. 8 shows a first example of a method for deriving a cortisol response.

FIG. 8 shows how the detected SCR pulses and (non-phasic) rises in tonic level dSCL are converted into a cortisol response. Module 90 calculates a weighted sum of the amplitude of the SCR signals and the dSCL amplitudes. The latter reflects the amplitude of the increase in skin conductance.

The SCR and dSCL detection events happen at irregular moments. The dSCL and SCR amplitudes are processed immediate after they become available.

A weighting is implemented in module 90 as the SCR signals are not always available (depending on skin measurement location) and dSCLs are not always fully reliable (due to thermal effects). The weight factor is thus derived from the quality of the data that has been used to detect the SCL rise. This quality factor can be used to qualify or to weight the dSCL contribution. The weighted values are integrated in integrator 92 over a 1 minute interval (other intervals are of course possible). After decimation in unit 94 to a 1 minute sample rate, the signal is convolved in convolution unit 96 with a standard cortisol response curve, as is described in US 20140288401 A1. The units 90, 92, 94,96 may together form part of a processor for calculating the cortisol response.

In order to prepare the input to the cortisol processing unit, the signal dSCL is defined as any rise in the skin conductance signal that is not attributable to a phasic response and hence does not qualify as SCR.

The analog to digital converter may have a fewer number of bits than has previously required in order to distinguish between tonic dSCL and phasic SCR components across a range of skin conductance values, for example it may be a 12 bit converter.

Figure 9:
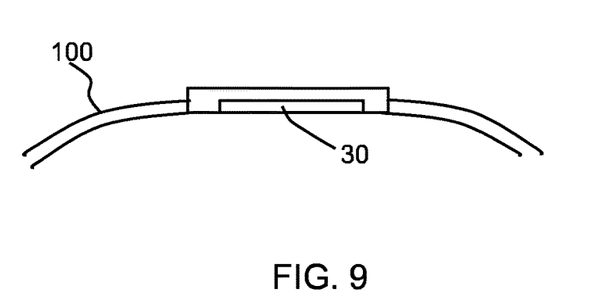
FIG. 9 shows the system of FIG. 5 implemented as part of a wrist mounted sensor device.

FIG. 9 shows the sensor (including at least the amplifier 30) implemented as part of a monitoring system comprising a wrist band 100. The sensor then mounted to contact the top of the wrist.

The monitoring system includes an output device for presenting information to the user. The output device may be a display which is part of the worn system, but it may instead be a wireless output signal which is provided to a wireless portable device of the user, such as a computer, smart phone or tablet.

One example of the use of the system is to providing advice to the user relating to required behavior for improving the quality of a next sleep period of the user. This is based on controlling the emotional state and physical exertion of the user before they sleep in order to obtain the best sleep outcome.

However, the system may be used for any other purpose, where separation of the skin response into phasic and tonic components is of interest. The invention can be used in any sensor systems using skin conductance as input such as emotional state estimators, lie detectors, health sensors.

Figure 10:
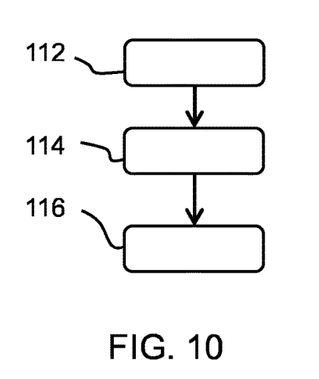
FIG. 10 shows a skin conductance sensing method.

FIG. 10 shows a method of measuring skin conductance. In step 112 signal amplification is carried out to convert a skin conductance into an analog output voltage. Non-linear amplification is carried out as explained above. In step 114 the analog output voltage is converted to a digital output signal. In step 116 the phasic skin response is extracted from the digital output signal. This method provides a digital output signal from which the different skin responses can be extracted in an efficient manner, regardless of the skin conductance level.

The example above is based on a logarithmic gain amplifier. However, other non-linear gain functions may be employed, for example exponential to power functions. The function may also not be perfectly logarithmic. For example, the resistor R3 in FIG. 3 (which may instead be in parallel with the skin conductance) is for draining input currents from the operational amplifier. The circuit behavior is not strictly logarithmic in the range of skin resistances close to R3 or the parallel resistor.

The sensor may be implemented without any analog filters or analog signal processing. Instead, the amplifier output is provided directly to the analog to digital converter. Some weak analog low pass filtering could however be useful to reduce 50 Hz mains interference or other external noise sources picked up by the system. Stronger filtering is not required, and as it could cause long delays after bad contact events.

The amplifier shown above is a single-ended design. The design may however make use of a differential amplifier. A differential implementation uses two single ended designs and the difference signal is processed. This enables suppression of noise, such as mains interference, but is of course a higher cost implementation.

The digital signal processor may receive other inputs to assist in the interpretation of the skin conductance measurements. For example, the system may include an accelerometer or other activity level sensor.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A sensor for measuring skin conductance, comprising:
an amplifier, wherein the amplifier is configured to convert the skin conductance into an analog output voltage;
an analog to digital converter, wherein the analog to digital converter is configured to convert the analog output voltage to a digital output signal; and
a digital processor, wherein the digital processor is configured to extract a phasic skin response from the digital output signal and increases in a tonic skin response,
wherein the amplifier has a logarithmic gain for generating an output signal which is a logarithm of the skin conductance, with a decreasing gain for increasing skin conductance values,
wherein the digital processor is adapted to extract the phasic skin response as a period of monotonic rise of the skin conductance with a rise time between a minimum and a maximum value, and
wherein the digital processor is adapted to identify increases in the tonic skin response as a rise of the skin conductance with a rise time longer than the maximum value and when no phasic skin response has been extracted.

2. The sensor of claim 1, wherein the digital processor is adapted to determine the rise time as the time from the skin conductance reaching a first level which is a multiple (1+k) of the skin conductance at the start of the monotonic rise to the end of the monotonic rise.

3. The sensor of claim 1, wherein the digital processor is adapted to extract the phasic skin response by:
detecting local maxima and minima in the digital output signal representing the skin conductance;
detecting rising edges in the digital output signal representing the skin conductance; and
identifying as the phasic skin response the rising edges which have a duration within a first range and an amplitude change within a second range, and
wherein the digital processor is adapted to extract increases in the tonic skin response by:
detecting rises in the digital output signal representing the skin conductance over a period at least longer than the maximum of the first range.

4. The sensor of claim 3, wherein the digital processor is adapted to extract increases in the tonic skin response by filtering out rises in the digital output signal representing the skin conductance corresponding to rising edges identified as phasic skin response.

5. The sensor of claim 1, wherein the amplifier comprises an operational amplifier having a reference voltage at a first input, a skin conductance between a second input and ground, and an output voltage at an output, wherein a feedback path is provided between the output and the second input, wherein the feedback path includes at least one diode.

6. The sensor of claim 1, further comprising a temperature measurement circuit.

7. The sensor of claim 1, further comprising a signal processing unit for filtering out or limiting the influence of skin conductance measurements during events of poor skin electrode contact and/or for filtering to reject or limiting the influence of false responses due to motion detected by an accelerometer.

8. The sensor of claim 1, further comprising a processor for calculating a cortisol response from the skin responses.

9. A monitoring system, comprising:
a sensor for measuring skin conductance, wherein the sensor comprises:
an amplifier, wherein the amplifier is configured to convert the skin conductance into an analog output voltage,
an analog to digital converter, wherein the analog to digital converter is configured to convert the analog output voltage to a digital output signal, and
a digital processor, wherein the digital processor is configured to extract a phasic skin response from the digital output signal and increases in a tonic skin response,
wherein the amplifier has a logarithmic gain for generating an output signal which is a logarithm of the skin conductance, with a decreasing gain for increasing skin conductance values,
wherein the digital processor is adapted to extract the phasic skin response as a period of monotonic rise of the skin conductance with a rise time between a minimum and a maximum value, and
wherein the digital processor is adapted to identify increases in the tonic skin response as a rise of the skin conductance with a rise time longer than the maximum value and when no phasic skin response has been extracted; and
a wrist band
wherein the sensor is mounted on the wrist band and configured for application to the top of a wrist.

10. The monitoring system of claim 9, further comprising an output device for providing advice to a user relating to required behavior for improving a quality of a next sleep period of the user.

11. A method, comprising:
performing signal amplification to convert a skin conductance into an analog output voltage;
converting the analog output voltage to a digital output signal; and
extracting a phasic skin response from the digital output signal and increases in a tonic skin response,
wherein the amplification is implemented with a logarithmic gain, generating an output signal which is a logarithm of the skin conductance, with a decreasing gain for increasing skin conductance,
wherein extracting the phasic skin response comprises extracting the phasic skin response as a period of monotonic rise of the skin conductance with a rise time between a minimum and a maximum value, and
wherein identifying increases in the tonic skin response comprises identifying increases in the tonic skin response as a rise of the skin conductance with a rise time longer than the maximum value and when no phasic response has been extracted.

12. The method of claim 11, wherein extracting the phasic skin response comprises:
- detecting local maxima and minima in the digital output signal representing the skin conductance;
- detecting rising edges in the digital output signal representing the skin conductance; and
- identifying as the phasic skin response the rising edges which have a duration within a first range and an amplitude change within a second range, and
- wherein extracting the tonic skin response comprises:
  - detecting rises in the digital output signal representing the skin conductance over a period at least longer than the maximum of the first range.

13. The method of claim 12, comprising extracting the tonic skin response by filtering out rises in the digital output signal representing the skin conductance corresponding to rising edges identified as phasic skin response.

14. The method of claim 11, further comprising:
- filtering out or limiting the influence of skin conductance measurements during events of poor skin electrode contact.

15. The method of claim 14, further comprising filtering to reject or limit the influence of false responses due to motion.

16. The method of claim 11, further comprising calculating a cortisol response from the skin responses.

17. The method of claim 11,
- performed by a wrist band sensor provided at a top of a wrist.

18. The method of claim 11, further comprising filtering to reject or limit the influence of false responses due to motion.

* * * * *